US006629924B2

(12) United States Patent  (10) Patent No.: US 6,629,924 B2
Aydelotte  (45) Date of Patent: Oct. 7, 2003

(54) ENHANCED ENDOTRACHEAL TUBE

(76) Inventor: Jayson D. Aydelotte, CMR 467 Box 5087, APO AE 09096

( * ) Notice: Subject to any disclaimer, the term of this patent is extended or adjusted under 35 U.S.C. 154(b) by 198 days.

(21) Appl. No.: 09/738,173

(22) Filed: Dec. 15, 2000

(65) Prior Publication Data

US 2002/0077527 A1 Jun. 20, 2002

(51) Int. Cl.$^7$ ................................................ A61M 1/00
(52) U.S. Cl. ........................ 600/120; 600/116; 600/130; 600/128; 600/139; 600/143; 600/153; 600/160; 600/178
(58) Field of Search ................................. 600/120, 112, 600/136, 123, 128, 130, 153, 143, 160, 139, 178, 116

(56) References Cited

U.S. PATENT DOCUMENTS

| 1,945,380 A | | 1/1934 | Russell ..................... 128/11 |
|---|---|---|---|
| 3,643,654 A | | 2/1972 | Felbarg ..................... 128/11 |
| 3,884,222 A | | 5/1975 | Moore ...................... 128/11 |
| 4,086,919 A | | 5/1978 | Bullard ..................... 128/11 |
| 4,306,547 A | | 12/1981 | Lowell ...................... 128/11 |
| 4,384,570 A | | 5/1983 | Roberts ...................... 128/4 |
| 4,584,998 A | * | 4/1986 | McGrail .................... 128/604 |
| 4,655,214 A | * | 4/1987 | Linder .................... 128/207.18 |
| 5,067,497 A | * | 11/1991 | Greear et al. ........... 128/207.15 |
| 5,119,811 A | * | 6/1992 | Inglis et al. ............ 128/207.14 |
| 5,501,652 A | | 3/1996 | Woods ......................... 600/200 |
| 5,638,812 A | * | 6/1997 | Turner ................... 128/207.14 |
| 5,733,242 A | * | 3/1998 | Rayburn et al. ............ 600/120 |
| 5,840,013 A | * | 11/1998 | Lee et al. ................... 600/114 |
| 5,846,183 A | * | 12/1998 | Chilcoat ..................... 600/136 |
| 5,873,818 A | | 2/1999 | Rothfels ..................... 600/188 |
| 5,941,816 A | * | 8/1999 | Barthel et al. ............. 600/120 |
| 6,113,588 A | * | 9/2000 | Duhaylongsod et al. ...... 606/15 |

* cited by examiner

Primary Examiner—Ira S. Lazarus
Assistant Examiner—Tu Cam Nguyen
(74) Attorney, Agent, or Firm—Jackie Lee Duke

(57) ABSTRACT

An enhanced endotracheal tube utilizing a fiber optic bundle positioned in its wall section to transmit light and a reflectively coated bore to transmit images is disclosed. Additional passages formed in the wall of the endotracheal tube are adapted to receive a stylette and to act as an air passage for inflating an inflatable cuff formed on the inner end of the endotracheal tube. The light transmitted through the fiber optic bundle aids in illuminating the patient's laryngeal area and the image is reflected along the reflectively coated bore to aid the physician in intubating the patient. Alternative embodiments using a bore with a sleeve having a different refractive index from that of the tube material and an enhanced endotracheal tube for use with children are shown.

16 Claims, 4 Drawing Sheets

ENHANCED ENDOTRACHEAL TUBE

BACKGROUND OF THE INVENTION

1. Field of the Invention

This invention relates to an enhanced endotracheal tube used by physicians for intubating a patient whose air passage is obstructed or is unable to breathe on his own. The enhanced endotracheal tube utilizes a fiber optic bundle and reflectively coated bore to aid the physician in visualizing the trachea and inserting the tube.

Endotracheal tubes are used by health care providers to provide a positive air passageway for a patient. Typically, the endotracheal tube is used when a person is undergoing surgery to provide for the administration of anesthesia or when mechanical ventilation of the lungs is necessary. Another time when the endotracheal tube is needed is when a person is injured and has lost the ability to breathe on their own. In this case time is of the essence in reestablishing a positive air passageway. However, often in these cases, it is difficult to see clearly the laryngeal area due to blood or other body fluids in the area. It would therefore be desirable to provide an external light source to the laryngeal area and reflectively coat the bore of the endotracheal tube to aid the physician in visualizing the area and ensure the endotracheal tube is properly inserted into the trachea and not the esophagus.

As is well known to those of ordinary skill in the art, in the human anatomy, the epiglottis lays over the glottis opening to the larynx to prevent food entering the trachea during eating. This necessitates the epiglottis be displaced from the glottal opening to allow the endotracheal tube to be inserted into the trachea. In a typical intubation an instrument known as a laryngoscope is inserted through the patient's mouth and used to hold the patient's epiglottis open and allow insertion of the endotracheal tube as noted above. Two commonly used types of laryngoscopes are the "Miller blade" having a straight blade and a "Macintosh" blade having a slightly curved blade.

The usual procedure for intubation of the trachea using a laryngoscope of either type described above is to place the patient in a horizonal position on their back, tilt the head back and open the mouth as widely as possible. The blade of the laryngoscope is then inserted through the mouth into the throat and used to hold the tongue and epiglottis out of the way so the glottis is exposed. The larynx of the patient may then be seen through the mouth. The endotracheal tube is then inserted, either through the mouth or nose, along the blade of the laryngoscope and into the glottis and trachea.

The problems with such instruments and procedures include possible further complications and injury to the spine or neck of patient's having spinal or neck injuries, damage to the patient's teeth in using the rigid blade of the laryngoscope or difficulty in viewing the glottis if a patient has any malformation of the jaw or throat areas. Laryngoscopes with added light sources were tried, but this added increased size. Similarly, the user was still limited to visualize the larynx by the exposure of the anatomy with the laryngoscope.

Therefore, there exists a need for an endotracheal tube that has an integral light source along with a reflectively coated bore to aid the physician during insertion. It is the construction and method of use of such an endotracheal tube to which the present invention is directed.

2. Description of Related Art

U.S. Pat. No. 3,643,654 to H. R. Felbarg discloses a laryngoscope with an electric light and mirror.

A laryngoscope with a light and mirror that is anatomically curved to aid insertion is disclosed in U.S. Pat. No. 3,884,222 to G. P. Moore.

U.S. Pat. No. 4,086,919 to J. R. Bullard describes a laryngoscope utilizing fiber optic bundles to transmit light and images. A laryngoscope using fiber optic bundles in a similar manner is disclosed in U.S. Pat. No. 4,306,547 to J. R. Lowell and includes a channel for inserting an endotracheal tube.

Another laryngoscope using fiber optic bundles, disclosed in U.S. Pat. No. 4,384,570 to J. T. Roberts, includes a pivotable handle.

U.S. Pat. No. 5,873,818 to N. L. Rothfels describes a laryngoscope with an optical system to provide a wide angle field of view.

SUMMARY OF THE INVENTION

The enhanced endotracheal tube of the present invention includes a flexible tube formed of a suitably flexible plastic material. The tube has an outer surface and a bore therethrough defining a wall section therebetween. In its preferred embodiment, the bore's axis is offset from the axis of the outer surface so that the wall section has a variable thickness. In the region of the thicker wall section, three passages are formed in the wall section. The passages extend axially through the thicker wall section and substantially parallel to the bore.

One of the passages is adapted to receive a fiber optic bundle, one is adapted to receive a stylette, and the third acts as an air passage. The passages may be of round, oval or other suitable cross sections as required to serve their intended purpose. An inflatable cuff is positioned adjacent the inner end, i.e., the end inserted into the patient's trachea. The inner end of the air passage extends to a point adjacent the inflatable cuff and then exits radially outwardly through the wall section to form a passageway through which air can be blown into the inflatable cuff. The outer end of the air passage has a tube connected thereto as in prior endotracheal tubes to allow inflation of the inflatable cuff.

The passage containing the fiber optic bundle extends the length of the endotracheal tube. The outer end of the fiber optic bundle extends away from the endotracheal tube and is connected to an external light source. The bore of the endotracheal tube is coated with a reflective coating to improve light and image transmission through the endotracheal tube and thereby aid the physician in viewing the trachea through the endotracheal tube.

In another embodiment, the bore of the endotracheal tube includes an inner sleeve constructed of a material such as plastic or fiber optic glass that has a different refractive index than the material of the tube. This allows for reflection of light and transmission of images along the length of the bore and inner sleeve. An endotracheal tube for use with children without an inflatable cuff is also shown.

One object of the present invention is to provide an enhanced endotracheal tube that uses a fiber optic bundle to transmit light into the patient's trachea and thereby aid the physician inserting the endotracheal tube.

Another object of the present invention is to provide an enhanced endotracheal tube with a reflectively coated bore to increase light transmission and thereby increase visualization through the endotracheal tube.

Other objects and advantages of the present invention are pointed out in the claims annexed hereto and form a part of this disclosure. A full and complete understanding of the invention may be had by reference to the accompanying drawings and description of the preferred embodiments.

BRIEF DESCRIPTION OF THE DRAWINGS

These and other objects and advantages of the present invention are set forth below and further made clear by reference to the drawings, wherein.

DESCRIPTION OF THE PREFERRED EMBODIMENTS

Figure 1:
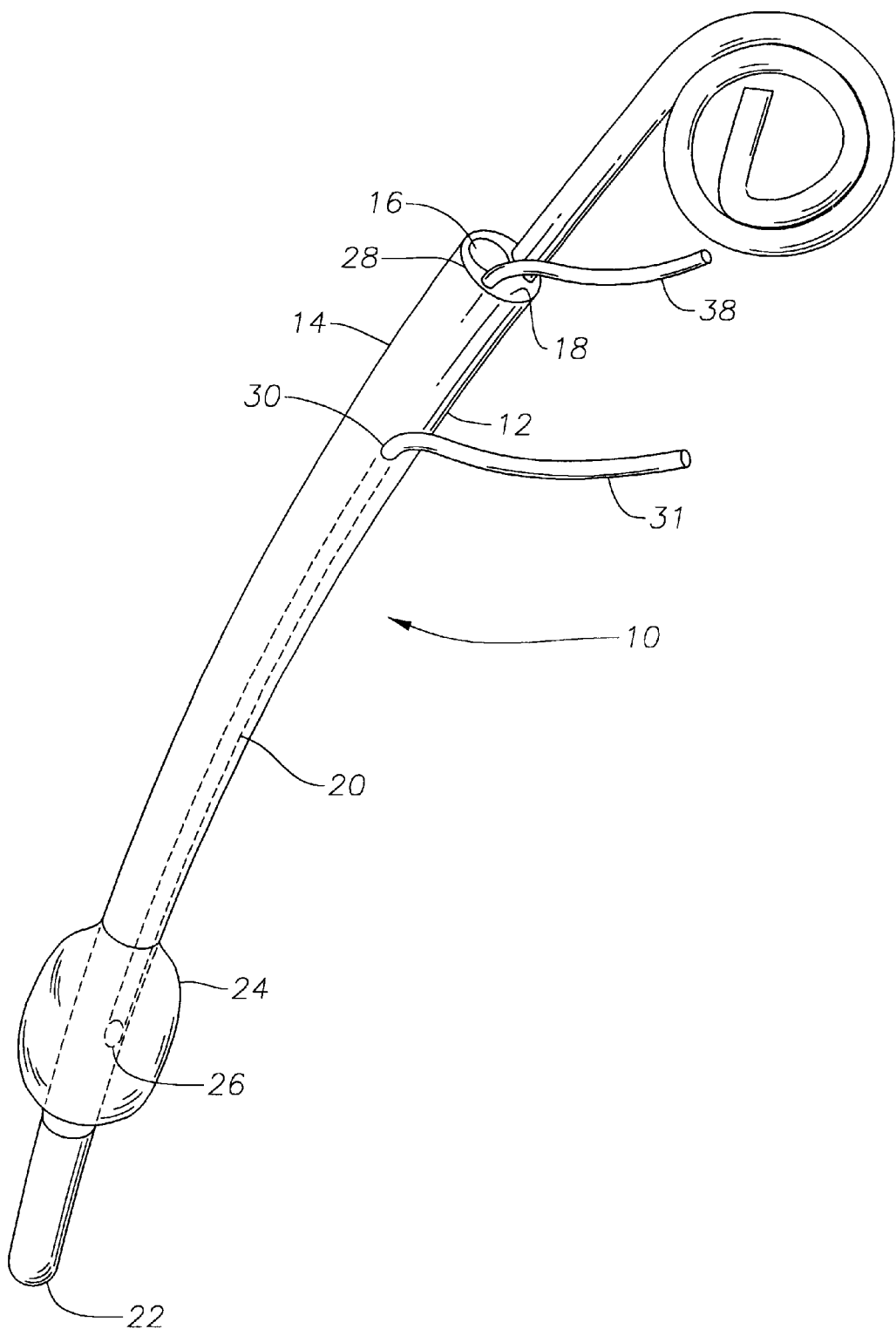
FIG. 1 is a perspective view of the enhanced endotracheal tube of the present invention with the stylette inserted and ready for installation.
Figure 2:
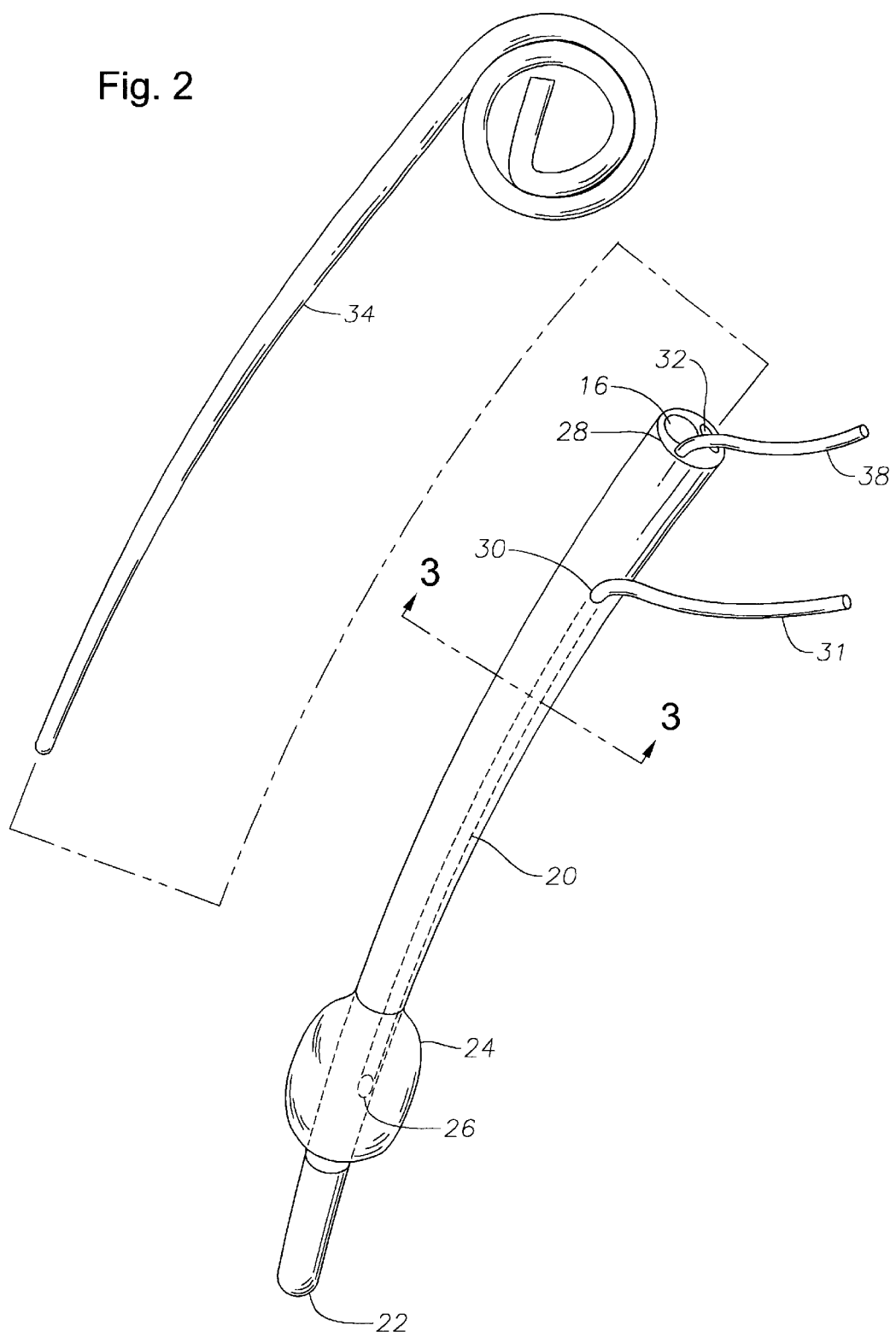
FIG. 2 is a perspective view of the endhanced endotracheal tube with the stylette removed.
Figure 3:
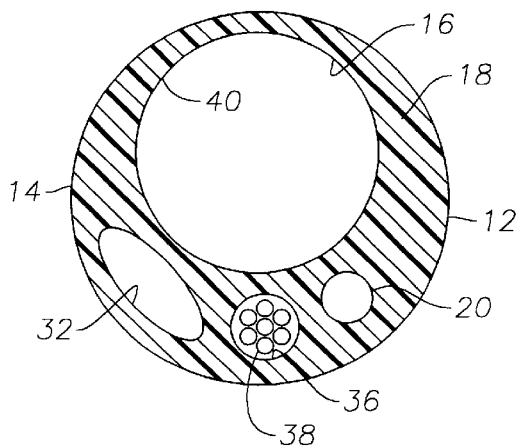
FIG. 3 is a cross sectional view of the enhanced endotracheal tube taken along lines 3—3 for FIG. 2.

With reference to the drawings, and particularly to FIG. 1, a perspective view of the enhanced endotracheal tube of the present invention is shown. The endotracheal tube is denoted generally by numeral 10. Endotracheal tube 10 comprises tube 12 having a plurality of passages formed therein. Tube 12 is formed of a suitably flexible and biocompatible material such as plastic. Tube 12 includes outer surface 14 and bore 16 therethrough to define wall section 18 therebetween. As can be seen more clearly in FIG. 3, bore 16 is substantially circular in cross section. The axis of bore 16 is offset from that of outer surface 14 such that wall section 18 varies in thickness. While outer surface 14 and bore 16 are shown with circular cross sections, those of ordinary skill in the art will understand that other suitable cross sections such as an oval could be used without departing from the scope of the present invention.

Air passage 20 formed in wall section 18 extends toward inner end 22 of tube 12, i.e., the end inserted into the patient's trachea. Air passage 20 extends to a point adjacent inflatable cuff 24 on outer surface 14 of tube 12 and adjacent inner end 22. Air passage 20 then exits radially outwardly through wall section 18 and port 26 to form a passageway through which air can be blown into inflatable cuff 24. As will be well known to those of ordinary skill in the art, inflatable cuff 24 is inflated after insertion into the patient's trachea to prevent movement of endotracheal tube 10. Air passage 20 extends upwardly to port 30 formed in wall section 18 of tube 12 to which is connected inflation tube 31 for connection to suitable apparatus well known to those of ordinary skill in the art to allow inflation of inflatable cuff 22.

Stylette passage 32 is formed in wall section 18 and has stylette 34 positioned therein. Stylette 34 is formed of suitably rigid material, as copper or aluminum or plastic, and is anatomically curved to aid the physician in inserting endotracheal tube 10 during intubation. In some cases, the physician will bend enhanced endotracheal tube 10 after stylette 34 is inserted into stylette passage 32 to accommodate patients with a malformed trachea. When stylette 34 is positioned in stylette passage 32, endotracheal tube 10 has sufficient rigidity so that it can be guided into position in the patient's trachea.

Fiber optic bundle passage 36 is formed in wall section 18 and extends the length of tube 12. Fiber optic bundle 38 is positioned within fiber optic bundle passage 36 and extends the length of endotracheal tube 10. Fiber optic bundle 38 extends from outer end 28 of tube 12 and is connected to a coherent light source (not shown). The light is transmitted through endotracheal tube 10 and onto the laryngeal area that the physician is guiding endotracheal tube 10 through.

Bore 16 of endotracheal tube 10 is coated with a light reflective coating 40 to aid in reflecting light along bore 16 and thereby transmit the image at inner 22 of tube 12 to outer end 28. This light reflective coating 40 may be silver or other suitable metal elements that may be applied to bore 16 to aid in light and image transmission. This will aid the physician in viewing the image and visualizing the trachea area to ensure endotracheal tube 10 is properly inserted.

Figure 4:
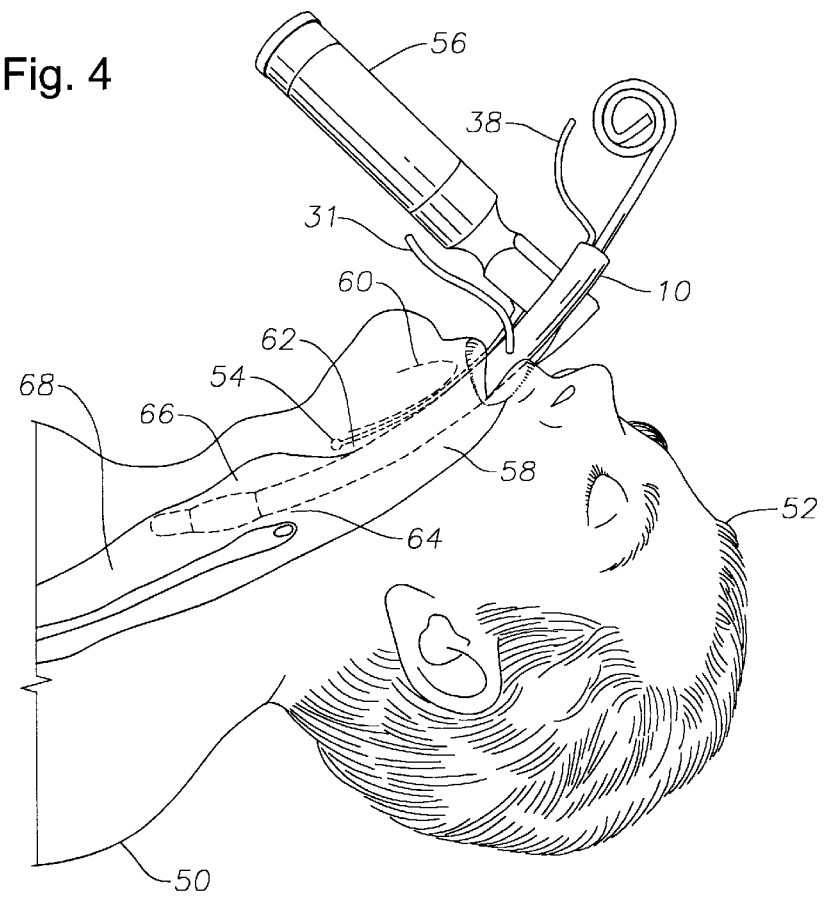
FIG. 4 is a side elevation view showing the enhanced endotracheal tube inserted in a patient's trachea.

FIG. 4 shows the use of endotracheal tube 10 to aid in visualizing the glottis and larynx of a patient. Patient 50 is in a supine position with head 52 tilted backward. Curved blade 54 of laryngoscope 56 is passed through oral passageway 58 and used to hold tongue 60 and epiglottis 62 and expose glottis 64. Light from an external light source (not shown) is transmitted through fiber optic bundle 38 to illuminate glottis 64 and larynx 66. The physician can look into bore 16 and see the reflection of light from inner end 22 to outer end 28 of endotracheal tube 10 and thereby view the aforementioned glottis 64 and larynx 66. Endotracheal tube 10 is thus slowly inserted past larynx 66 into trachea 68, aided by the illumination and visualization possible through bore 16. Once inserted, stylette 34 and laryngoscope 56 are removed and inflatable cuff 24 inflated through air passage 20 and inflation tube 31 to anchor endotracheal tube 10 within trachea 68.

Figure 5:
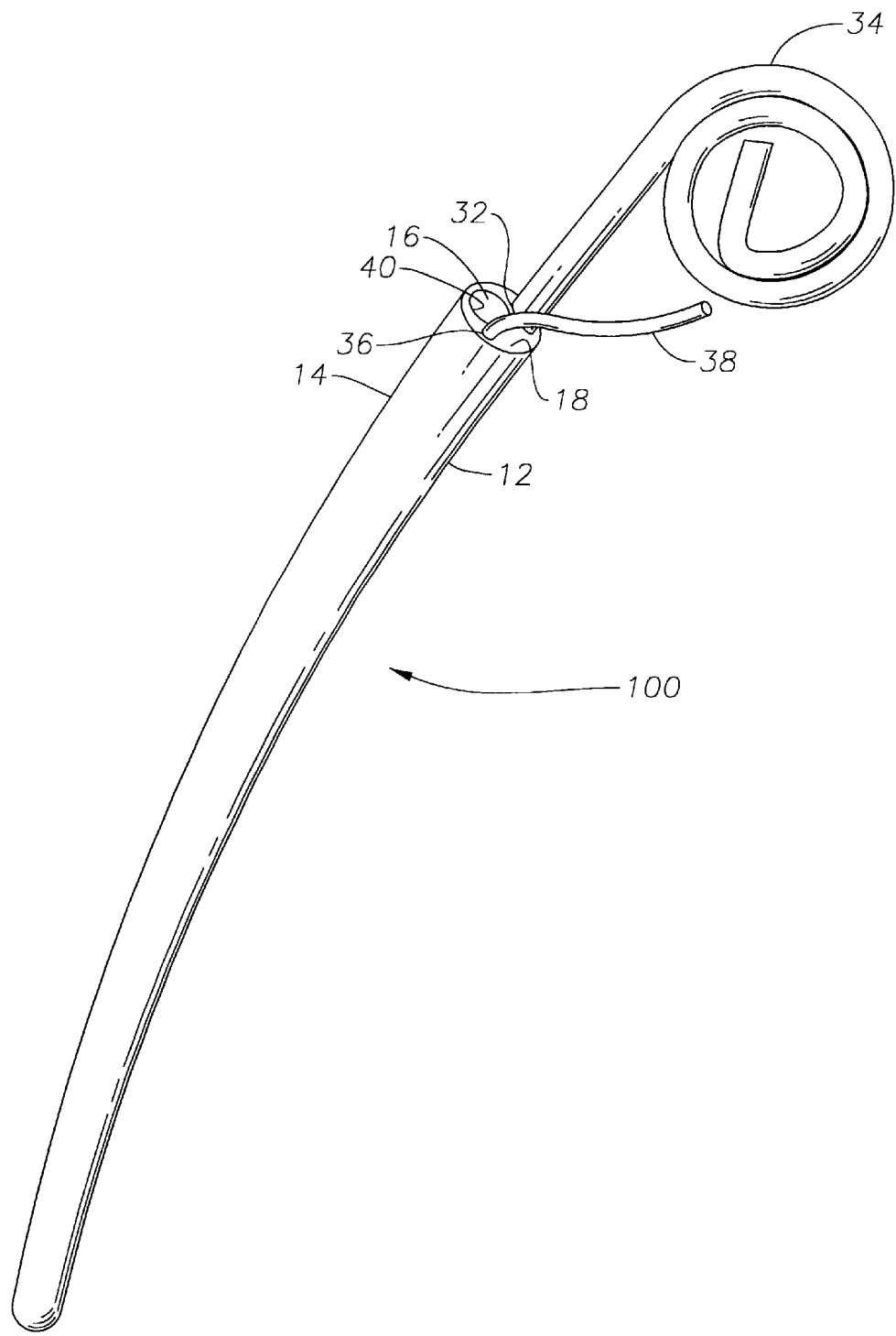
FIG. 5 is a perspective view of a second embodiment of the enhanced endotracheal tube of the present invention particularly suited for use with children with the stylette inserted and ready for installation.

FIG. 5 shows a perspective view of a second embodiment of the enhanced endotracheal tube of the present invention that is particularly suited for use with children. Due to the relatively small size of the trachea of children, the inflatable cuff of the first embodiment typically is not needed. Such an endotracheal tube is denoted generally by numeral 100. Those items which are the same as in the first embodiment retain their numerical designations. Endotracheal tube 100 comprises tube 12 having a plurality of passages formed therein and is formed of a suitably flexible and biocompatible material such as plastic. Tube 12 includes outer surface 14 and bore 16 therethrough to define wall section 18 therebetween.

Stylette passage 32 is formed in wall section 18 and has stylette 34 positioned therein. Stylette 34 functions in all respects as in the first embodiment. Fiber optic bundle passage 36 is formed in wall section 18 and extends the length of tube 12. Fiber optic bundle 38 is positioned within fiber optic bundle passage 36 and extends the length of endotracheal tube 100. Fiber optic bundle 38 extends the length of tube 12 and is connected to a coherent light source (not shown). The light is transmitted through endotracheal tube 100 and onto the laryngeal area that the physician is guiding endotracheal tube 100 through.

Bore 16 of endotracheal tube 100 is coated with a light reflective coating 40 as in the first embodiment to aid in reflecting light and transmit images along bore 16. This will aid the physician in viewing the image and visualizing the trachea area to ensure endotracheal tube 100 is properly inserted. In all other respects, endotracheal tube 100 functions the same as first embodiment endotracheal tube 10.

Figure 6:
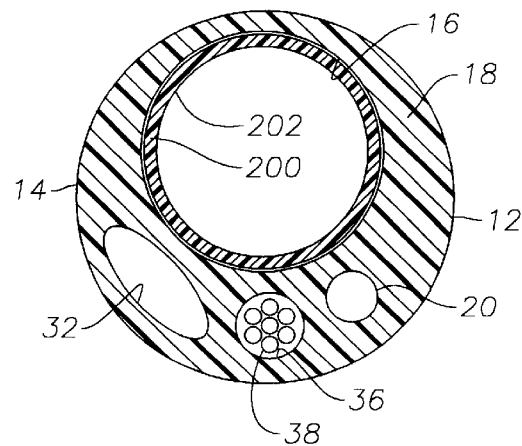
FIG. 6 is a cross sectional view of the enhanced endotracheal tube with a differential refractive index.

An alternate construction for bore 16 of endotracheal tubes 10 and 100 is shown in FIG. 6. Those items which are the same as in the previous embodiments retain their numerical designations. Bore 16 has inner sleeve 200 inserted therein. Inner sleeve 200 may be formed of a plastic material or fiber optic glass material and has a different refractive index from that of the plastic material of which tube 12 is constructed. This difference in refractive indices reflects light shown into bore 16 along inner surface 202 of inner sleeve 200. Thus, as in the previous embodiments, a light reflective surface is formed that enhances the transmission of light and images through bore 16 to aid the physician in visualizing the trachea and intubating the patient.

The novel method of use and construction of my enhanced endotracheal tube will be readily understood from the foregoing description and it will be seen that I have provided an enhanced endotracheal tube that uses a fiber optic bundle to transmit light into the patient's trachea and a reflectively coated bore to increase light transmission and thereby increase visualization through the endotracheal tube, thereby aiding the physician inserting the endotracheal tube. Furthermore, while the invention has been shown and described with respect to certain preferred embodiments, it is obvious that equivalent alterations and modifications will occur to others skilled in the art upon the reading and understanding of the specification. The present invention includes all such equivalent alterations and modifications, and is limited only by the scope of the appended claims.

What is claimed is:

1. An enhanced endotracheal tube for endotracheal intubation, comprising:
   a flexible tube having an outer surface and a bore therethrough defining a wall section therebetween;
   a plurality of passages disposed in said wall section, said plurality of passages extending axially through said wall section and substantially parallel to said bore;
   at least one of said passages adapted to receive a fiber optic bundle;
   an inflatable cuff positioned adjacent one end of said flexible tube;
   at least one of said passages connected through said wall section to said inflatable cuff to allow inflation of said cuff;
   said bore of said flexible tube is coated with a light reflective coating to enhance light and image transmission along said bore;
   said at least one of said passages adapted to receive a fiber optic bundle is connected to an external light source;
   at least one of said passages is adapted to receive a stylette, said stylette is malleable and may be anatomically formed to aid a user in inserting said enhanced endotracheal tube during intubation;
   said stylette is removable from said endotracheal tube after intubation; and,
   said wall section has a variable thickness.

2. An enhanced endotracheal tube for endotracheal intubation, according to claim 1 wherein:
   said outer surface and said bore of said flexible tube have non-circular cross sections.

3. An enhanced endotracheal tube for endotracheal intubation, according to claim 2 wherein:
   said plurality of passages disposed in said wall section have non-circular cross sections.

4. An enhanced endotracheal tube for endotracheal intubation, according to claim 2 wherein:
   said plurality of passages disposed in said wall section have circular cross sections.

5. An enhanced endotracheal tube for endotracheal intubation, comprising:
   a flexible tube having an outer surface and a bore therethrough defining a wall section therebetween,
   an inner sleeve disposed in said bore, said inner sleeve and said flexible tube bore having different refractive indices thereby forming a light reflective surface on the inner surface of said inner sleeve;
   a plurality of passages disposed in said wall section, said plurality of passages extending axially through said wall section and substantially parallel to said bore;
   at least one of said passages adapted to receive a fiber optic bundle;
   an inflatable cuff positioned adjacent one end of said flexible tube;
   at least one of said passages connected through said wall section to said inflatable cuff to allow inflation of said cuff;
   said at least one of said passages adapted to receive a fiber optic bundle is connected to an external light source;
   at least one of said passages is adapted to receive a stylette, said stylette is malleable and may be anatomically formed to aid a user in inserting said enhanced endotracheal tube during intubation;
   said stylette is removable from said endotracheal tube after intubation; and,
   said wall section has a variable thickness.

6. An enhanced endotracheal tube for endotracheal intubation, according to claim 5 wherein:
   said outer surface and said bore of said flexible tube have non-circular cross sections.

7. An enhanced endotracheal tube for endotracheal intubation, according to claim 6 wherein:
   said plurality of passages disposed in said wall section have non-circular cross sections.

8. An enhanced endotracheal tube for endotracheal intubation, according to claim 6 wherein:
   said plurality of passages disposed in said wall section have circular cross sections.

9. An enhanced endotracheal tube for endotracheal intubation, comprising:
   a flexible tube having an outer surface and a bore therethrough defining a wall section therebetween;
   a plurality of passages disposed in said wall section, said plurality of passages extending axially through said wall section and substantially parallel to said bore;
   at least one of said passages adapted to receive a fiber optic bundle;
   said bore of said flexible tube is coated with a light reflective coating to enhance light and image transmission along said bore;
   said at least one of said passages adapted to receive a fiber optic bundle is connected to an external light source
   at least one of said passages is adapted to receive a stylette, said stylette is malleable and may be anatomically formed to aid a user in inserting said enhanced endotracheal tube during intubation;

said stylette is removable from said endotracheal tube after intubation; and, said wall section has a variable thickness.

10. An enhanced endotracheal tube for endotracheal intubation, according to claim 9 wherein:

said outer surface and said bore of said flexible tube have non-circular cross sections.

11. An enhanced endotracheal tube for endotracheal intubation, according to claim 10 wherein:

said plurality of passages disposed in said wall section have non-circular cross sections.

12. An enhanced endotracheal tube for endotracheal intubation, according to claim 10 wherein:

said plurality of passages disposed in said wall section have circular cross sections.

13. An enhanced endotracheal tube for endotracheal intubation, comprising:

a flexible tube having an outer surface and a bore therethrough defining a wall section therebetween, an inner sleeve disposed in said bore, said inner sleeve and said flexible tube bore having different refractive indices thereby forming a light reflective surface on the inner surface of said inner sleeve;

a plurality of passages disposed in said wall section, said plurality of passages extending axially through said wall section and substantially parallel to said bore;

at least one of said passages adapted to receive a fiber optic bundle;

said at least one of said passages adapted to receive a fiber optic bundle is connected to an external light source;

at least one of said passages is adapted to receive a stylette, said stylette is malleable and may be anatomically formed to aid a user in inserting said enhanced endotracheal tube during intubation;

said stylette is removable from said endotracheal tube after intubation; and, said wall section has a variable thickness.

14. An enhanced endotracheal tube for endotracheal intubation, according to claim 13 wherein:

said outer surface and said bore of said flexible tube have non-circular cross sections.

15. An enhanced endotracheal tube for endotracheal intubation, according to claim 14 wherein:

said plurality of passages disposed in said wall section have non-circular cross sections.

16. An enhanced endotracheal tube for endotracheal intubation, according to claim 14 wherein:

said plurality of passages disposed in said wall section have circular cross sections.

* * * * *